(12) United States Patent
Kim

(10) Patent No.: US 12,097,038 B2
(45) Date of Patent: Sep. 24, 2024

(54) METHOD AND APPARATUS FOR DETERMINING DEGREE OF DEMENTIA OF USER

(71) Applicant: Aible Therapeutics Co., Ltd., Seoul (KR)

(72) Inventor: Hyung Jun Kim, Seoul (KR)

(73) Assignee: Aible Therapeutics Co., Ltd., Seoul (KR)

(*) Notice: Subject to any disclaimer, the term of this patent is extended or adjusted under 35 U.S.C. 154(b) by 0 days.

(21) Appl. No.: 17/608,592

(22) PCT Filed: Sep. 2, 2021

(86) PCT No.: PCT/KR2021/011848
§ 371 (c)(1),
(2) Date: Nov. 3, 2021

(87) PCT Pub. No.: WO2022/050719
PCT Pub. Date: Mar. 10, 2022

(65) Prior Publication Data
US 2023/0210440 A1    Jul. 6, 2023

(30) Foreign Application Priority Data
Sep. 4, 2020 (KR) .................. 10-2020-0113333

(51) Int. Cl.
*G06F 40/40* (2020.01)
*A61B 5/00* (2006.01)
*G16H 50/20* (2018.01)

(52) U.S. Cl.
CPC .......... *A61B 5/4088* (2013.01); *A61B 5/4803* (2013.01); *A61B 5/7264* (2013.01); *A61B 5/7267* (2013.01); *A61B 5/742* (2013.01); *G16H 50/20* (2018.01)

(58) Field of Classification Search
CPC ........ A61B 5/4088; G06F 40/40; G10L 15/22
See application file for complete search history.

(56) References Cited

U.S. PATENT DOCUMENTS

| | | | |
|---|---|---|---|
| 2015/0265205 A1* | 9/2015 | Rosenbek | A61B 7/00 600/586 |
| 2018/0366143 A1* | 12/2018 | Ashoori | G16H 40/63 |
| 2019/0074028 A1* | 3/2019 | Howard | G10L 25/21 |
| 2019/0108316 A1* | 4/2019 | Anumalasetty | G16H 10/20 |
| 2021/0303866 A1* | 9/2021 | Chen | G06V 10/82 |

FOREIGN PATENT DOCUMENTS

| | | | |
|---|---|---|---|
| CN | 107705806 A | * | 2/2018 |
| KR | 101936302 B1 | * | 1/2019 |
| KR | 102001398 B1 | | 7/2019 |

OTHER PUBLICATIONS

International Conference on Data Science, Machine Learning and Statistics Proceedings Book (Jun. 29, 2019).

* cited by examiner

*Primary Examiner* — Daniel Abebe
(74) *Attorney, Agent, or Firm* — JCIPRNET

(57) ABSTRACT

In order to determine a degree of dementia of a user, contents are output through a user terminal, a voice of the user for a content acquired by a microphone of the user terminal is received, a spectrogram image is generated by visualizing the voice, and the degree of dementia of the user is determined by means of a convolutional neural network (CNN) and a deep neural network (DNN) based on the spectrogram image.

13 Claims, 15 Drawing Sheets

METHOD AND APPARATUS FOR DETERMINING DEGREE OF DEMENTIA OF USER

CROSS-REFERENCES TO RELATED APPLICATIONS

This application is a U.S. national phase application, pursuant to 35 U.S.C. § 371, of PCT/KR2021/011848, filed Sep. 2, 2021, designating the United States, which claims priority to Korean Application No. 10-2020-0113333, filed Sep. 4, 2020. The entire contents of the aforementioned patent applications are incorporated herein by this reference.

TECHNICAL FIELD

The following description relates to a technique of determining a degree of dementia of a user, and more particularly to an apparatus and a method for determining a degree of dementia of a user based on a voice of the user.

BACKGROUND ART

Dementia is the most serious disease in the life of the old age together with the aging of society and shows a rapid increase in the past 10 years. Further, the social and economic cost is also rapidly increasing. The dementia prevents a patient from living independently and causes great pain not only for the patient's own life, but also for the family who cares for the patient, due to disappearance or suicide. Early diagnosis and appropriate treatment of the dementia may prevent or delay further cognitive decline, but the existing early diagnosis of the dementia has problems. In the related art, the patient needs to visit specialized medical institutions such as hospitals. Therefore, among patients who feel that their forgetfulness has worsened and visit the hospital, many of them have already progressed to mild cognitive impairment (MCI) or Alzheimer's disease (AD). Further, the neurocognitive function test (SNSB-II or CERAD-K) for diagnosis may be highly reliable only through a medical expert having sufficient experience and knowhow. Further, the magnetic resonance imaging (MRI), single photon emission computed tomography (SPECT), positron emission tomography (PET), and cerebrospinal fluid analysis are expensive and are very inconvenient to the patient who receives the diagnosis.

DISCLOSURE OF THE INVENTION

Technical Goals

An exemplary embodiment may provide an apparatus and a method for determining a degree of dementia of a user.

An exemplary embodiment may provide an apparatus and a method for determining a degree of dementia of a user based on a voice of the user.

Technical Solutions

According to an aspect, a method for determining a degree of dementia of a user, performed by an electronic device includes outputting a first content which is produced in advance to determine a degree of dementia of a user through a user terminal; receiving a first voice of the user for the first content acquired by a microphone of the user terminal; outputting a second content which is produced in advance through the user terminal; receiving a second voice of the user for the second content acquired by the microphone; generating a first spectrogram image by visualizing at least one characteristic of the first voice; generating a second spectrogram image by visualizing at least one characteristic of the second voice; generating a predetermined number of first features for the first voice by inputting the first spectrogram image to a previously updated first convolutional neural network (CNN); generating a predetermined number of second features for the second voice by inputting the second spectrogram image to a previously updated second CNN; determining a predetermined number of target features among the first features and the second features; and determining a degree of dementia of the user by inputting the target features to a previously updated deep neural network (DNN), and the determined degree of dementia is output through the user terminal.

The first content may include an instruction for receiving the first voice.

The first content is one of a content of causing a user to repeat a sentence, a content of naming an output image, a content of describing an output image, a content for language fluency, a content for calculating numbers, and a content of leading story telling.

The generating of a first spectrogram image by visualizing at least one characteristic of the first voice may include: generating the first spectrogram image for the first voice by means of a librosa tool.

A size of the first spectrogram image and a size of the second spectrogram image may be equal to each other.

The first CNN may be updated in advance based on a VGG16 model.

The first CNN includes an input layer and five convolution layer blocks, but does not include a fully connected layer and a softmax to generate the first features for the first spectrogram image.

The method for determining a degree of dementia may further include updating the first CNN.

The updating of the first CNN includes: receiving a first test voice of a test user for the first content; generating a first test spectrogram image by visualizing at least one characteristic of the first test voice in which a ground truth (GT) dementia degree of the test user is labeled to the first test spectrogram image; determining a first test dementia degree of the test user by inputting the first test spectrogram image to a first fully CNN in which the first fully CNN includes an input layer, one or more convolution layer blocks, a fully connected layer, and a softmax, and updating the first fully CNN based on the first test dementia degree and the GT dementia degree, and the first CNN may include only the input layer and the one or more convolution layer blocks among layers of the updated first fully CNN.

The method for determining a degree of dementia may further include updating the DNN after completing the updating of a plurality of CNNs including the first CNN and the second CNN.

The updating of the DNN may include: determining a predetermined number of test target features among a predetermined number of first test features generated based on a first test spectrogram image and a predetermined number of second test features generated based on a second test spectrogram image in which the GT dementia degree of the test user is labeled to the test target features; determining a second test dementia degree of the test user by inputting the test target features to the DNN; and updating the DNN based on the second test dementia degree and the GT dementia degree.

The updating of the DNN further may include: verifying the test target features by means of a K-fold cross-validation in which K is a natural number of 2 or larger, and when the test target features are not verified, the first CNN and the second CNN may be re-updated.

The verifying of the test target features by means of a K-fold cross-validation may include: dividing sets of the test target features into K groups; generating K test DNNs by updating K initial DNNs based on the K groups; and verifying the test target features based on an accuracy of the K test DNNs.

According to another aspect, an electronic device for determining a degree of dementia of a user includes a memory in which a program of determining a degree of dementia of a user is recorded; and a processor which executes the program, and the program executes: outputting a first content which is produced in advance to determine a degree of dementia of a user through a user terminal; receiving a first voice of the user for the first content acquired by a microphone of the user terminal; outputting a second content which is produced in advance through the user terminal; receiving a second voice of the user for the second content acquired by the microphone; generating a first spectrogram image by visualizing at least one characteristic of the first voice; generating a second spectrogram image by visualizing at least one characteristic of the second voice; generating a predetermined number of first features for the first voice by inputting the first spectrogram image to a previously updated first convolutional neural network (CNN); generating a predetermined number of second features for the second voice by inputting the second spectrogram image to a previously updated second CNN; determining a predetermined number of target features among the first features and the second features; and determining a degree of dementia of the user by inputting the target features to a previously updated deep neural network (DNN), and the determined degree of dementia is output through the user terminal.

According to still another aspect, a method for updating a convolutional neural network (CNN) used to determine a degree of dementia of a user, executed by an electronic device includes: outputting a first content which is produced in advance to determine a degree of dementia of a user through a user terminal; receiving a first test voice of a test user for the first content; generating a first test spectrogram image by visualizing at least one characteristic of the first test voice in which a ground truth (GT) dementia degree of the test user is labeled to the first test spectrogram image; determining a test dementia degree of the test user by inputting the first test spectrogram image to a fully CNN in which the fully CNN includes an input layer, one or more convolution layer blocks, a fully connected layer, and a softmax; and updating the fully CNN based on the test dementia degree and the GT dementia degree, and the CNN includes only the input layer and the one or more convolution layer blocks among layers of the updated fully CNN.

According to still another aspect, an electronic device which updates a convolutional neural network (CNN) used to determine a degree of dementia of a user includes: a memory in which a program of updating the CNN is recorded; and a processor which executes the program, the program executes: outputting a first content which is produced in advance to determine a degree of dementia of a user through a user terminal; receiving a first test voice of a test user for the first content; generating a first test spectrogram image by visualizing at least one characteristic of the first test voice in which a ground truth (GT) dementia degree of the test user is labeled to the first test spectrogram image; determining a test dementia degree of the test user by inputting the first test spectrogram image to a fully CNN in which the fully CNN includes an input layer, one or more convolution layer blocks, a fully connected layer, and a softmax; and updating the fully CNN based on the test dementia degree and the GT dementia degree, and the CNN includes only the input layer and the one or more convolution layer blocks among layers of the updated fully CNN.

Effects

An apparatus and a method for determining a degree of dementia of a user may be provided.

An apparatus and a method for determining a degree of dementia of a user based on a voice of the user may be provided.

BEST MODE FOR CARRYING OUT THE INVENTION

Figure 1:
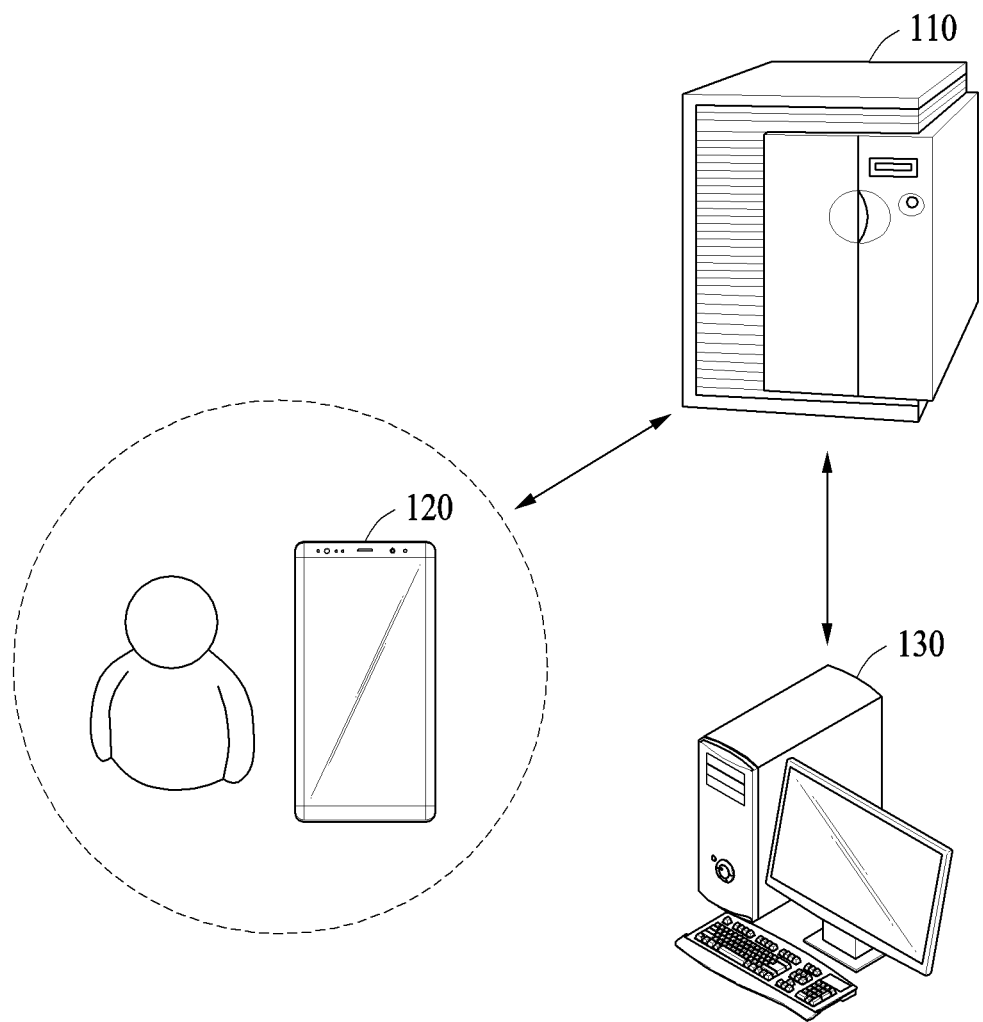
FIG. 1 is a diagram of a system for determining a degree of dementia of a user according to an example.

Hereinafter, exemplary embodiments will be described in detail with reference to the accompanying drawings. However, the scope of the patent application will not be limited or restricted to exemplary embodiments below. In each of the drawings, like reference numerals denote like elements.

Exemplary embodiments to be described below may be modified in various ways. It should be understood that exemplary embodiments to be described below are not intended to limit the examples, but include all changes, equivalents, and alternatives to them.

Terms used in the exemplary embodiment are used only to describe a specific exemplary embodiment, but are not intended to limit the exemplary embodiment. A singular form may include a plural form if there is not clearly opposite meaning in the context. In the present specification, it should be understood that terminology "include" or "have" indicates that a feature, a number, a step, an operation, a component, a part or the combination thoseof described in the specification is present, but do not exclude a possibility of presence or addition of one or more other features, numbers, steps, operations, components, parts or combinations thoseof, in advance.

If it is not contrarily defined, all terms used herein including technological or scientific terms have the same meaning as those generally understood by a person with ordinary skill in the art. Terms defined in a generally used dictionary shall be construed that they have meanings matching those in the context of a related art, and shall not be construed in ideal or excessively formal meanings unless they are clearly defined in the present application.

In description with reference to accompanying drawings, the same components are denoted by the same reference numerals regardless of the reference numeral and a duplicated description thereof will be omitted. In description of an exemplary embodiment, if it is determined that a detailed description for a related art may unnecessarily blur the gist of the exemplary embodiment, the detailed description will be omitted.

FIG. 1 is a diagram of a system for determining a degree of dementia of a user according to an example.

According to an aspect, a system for determining a degree of dementia of a user may include an electronic device 110 which determines a degree of dementia of a user, a user terminal 120 which outputs contents, and a monitoring terminal 130 of a medical institution. For example, the electronic device 110 may be a server.

The electronic device 110 may provide previously produced contents to the user terminal 120 to determine a degree of dementia of the user. For example, the contents may be contents for acquiring a voice from the user. The contents will be described below in detail with reference to FIGS. 5 and 6.

The user terminal 120 is connected to the electronic device 110 via off-line or on-line to communicate with each other. The electronic device 110 provides the contents to the user terminal 120 and the user terminal 120 outputs the contents to the user through a display. The user terminal 120 may acquire a voice of the user as a reaction for the contents through a microphone and transmit the acquired voice to the electronic device 110.

The electronic device 110 may determine the degree of dementia of the user based on the acquired voice of the user and transmit the determined degree of dementia to the user terminal 120.

The user terminal 120 may be a mobile terminal such as a tablet or a smartphone. When the user terminal 120 is a mobile terminal, the user may measure a degree of dementia at a low cost without being restricted by a time and a location.

The electronic device 110 may transmit the voice and the degree of dementia of the user to the monitoring terminal 130. For example, a user of the monitoring terminal 130 may be a doctor and the doctor may adjust the contents provided to the user based on the transmitted information.

Hereinafter, a method for determining a degree of dementia of the user will be described in more detail with reference to FIGS. 2 to 17.

Figure 2:
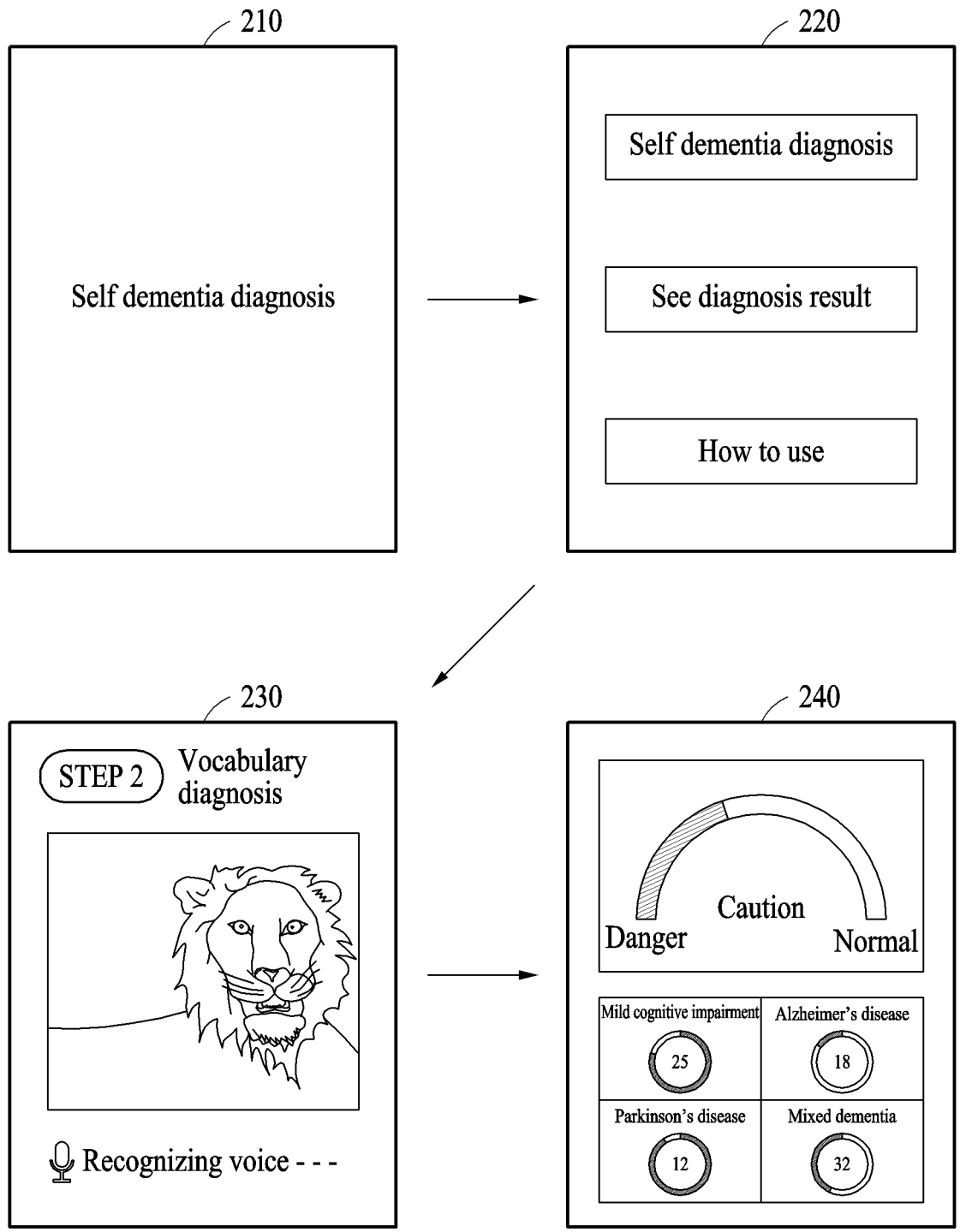
FIG. 2 illustrates images output to a user terminal to determine a degree of dementia of a user according to an example.

FIG. 2 illustrates images output to a user terminal to determine a degree of dementia of a user according to an example.

Following images 210 to 240 may be images of applications for determining a degree of dementia. For example, the user of the electronic device 110 may produce and distribute the application and the user may execute the application by means of the user terminal 120.

A first image 210 is a starting screen of an application.

A second image 220 displays functions supported by the application.

A third image 230 is an example of contents provided to the user. A plurality of contents may be provided to the user.

A fourth image 240 displays a determined degree of dementia of the user. For example, normal, mild cognitive impairment (MCI), or Alzheimer's disease (AD) which is determined as a degree of dementia of the user may be output. A comprehensive judgment may be output as well as a degree of warning for individual disease.

Figure 3:
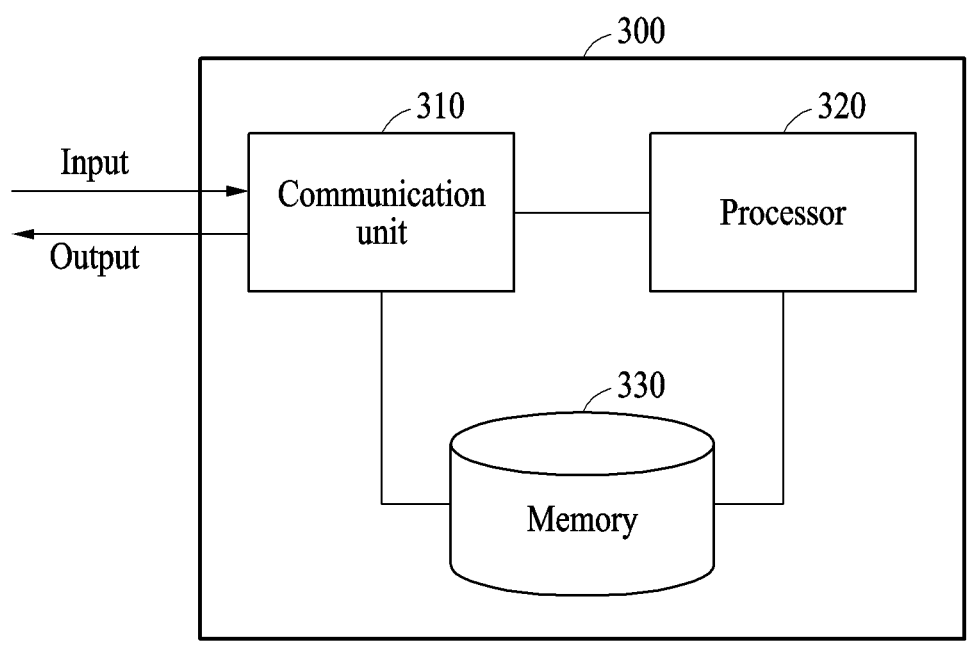
FIG. 3 is a diagram of an electronic device for determining a degree of dementia of a user according to an exemplary embodiment.

FIG. 3 is a diagram of an electronic device for determining a degree of dementia of a user according to an exemplary embodiment.

The electronic device 300 includes a communication unit 310, a processor 320, and a memory 330. For example, the electronic device 300 may be the electronic device 110 which has been described above with reference to FIG. 1.

The communication unit 310 is connected to the processor 320 and the memory 330 to transmit and receive data. The communication unit 310 may be connected to the other external device to transmit and receive data. Hereinafter, the expression of transmitting and receiving "A" means transmitting and receiving of "information or data indicating A."

The communication unit 310 may be implemented by a circuitry in the electronic device 300. For example, the communication unit 310 may include an internal bus and an external bus. As another example, the communication unit 310 may be an element which connects the electronic device 300 and an external device. The communication unit 310 may be an interface. The communication unit 310 receives data from the external device to transmit the data to the processor 320 and the memory 330.

The processor 320 processes data received by the communication unit 310 and data stored in the memory 330. The "processor" may be a data processing device which is implemented by hardware having a circuit having a physical structure for executing desired operations. For example, the desired operations may include codes or instructions included in the program. For example, the data processing device implemented by hardware may include a microprocessor, a central processing unit, a processor core, a multi-core processor, a multiprocessor, an application-specific integrated circuit (ASIC), and a field programmable gate array (FPGA).

The processor 320 executes computer readable codes (for example, software) stored in a memory (for example, the memory 330) and instructions induced by the processor 320.

The memory 330 stores data received by the communication unit 310 and data processed by the processor 320. For example, the memory 330 may store a program (or an application or software). The stored program may be a set of syntaxes which are coded to determine a degree of dementia of the user to be executable by the processor 320.

According to an aspect, the memory 330 includes one or more of volatile memories, non-volatile memories, random access memories (RAM), flash memories, hard disk drives, and optical disk drives.

The memory 330 stores an instruction set (for example, software) which causes the electronic device 300 to operate. The instruction set which causes the electronic device 300 to operate is executed by the processor 320.

The communication unit 310, the processor 320, and the memory 330 will be described below in detail with reference to FIGS. 4 to 17.

Figure 4:
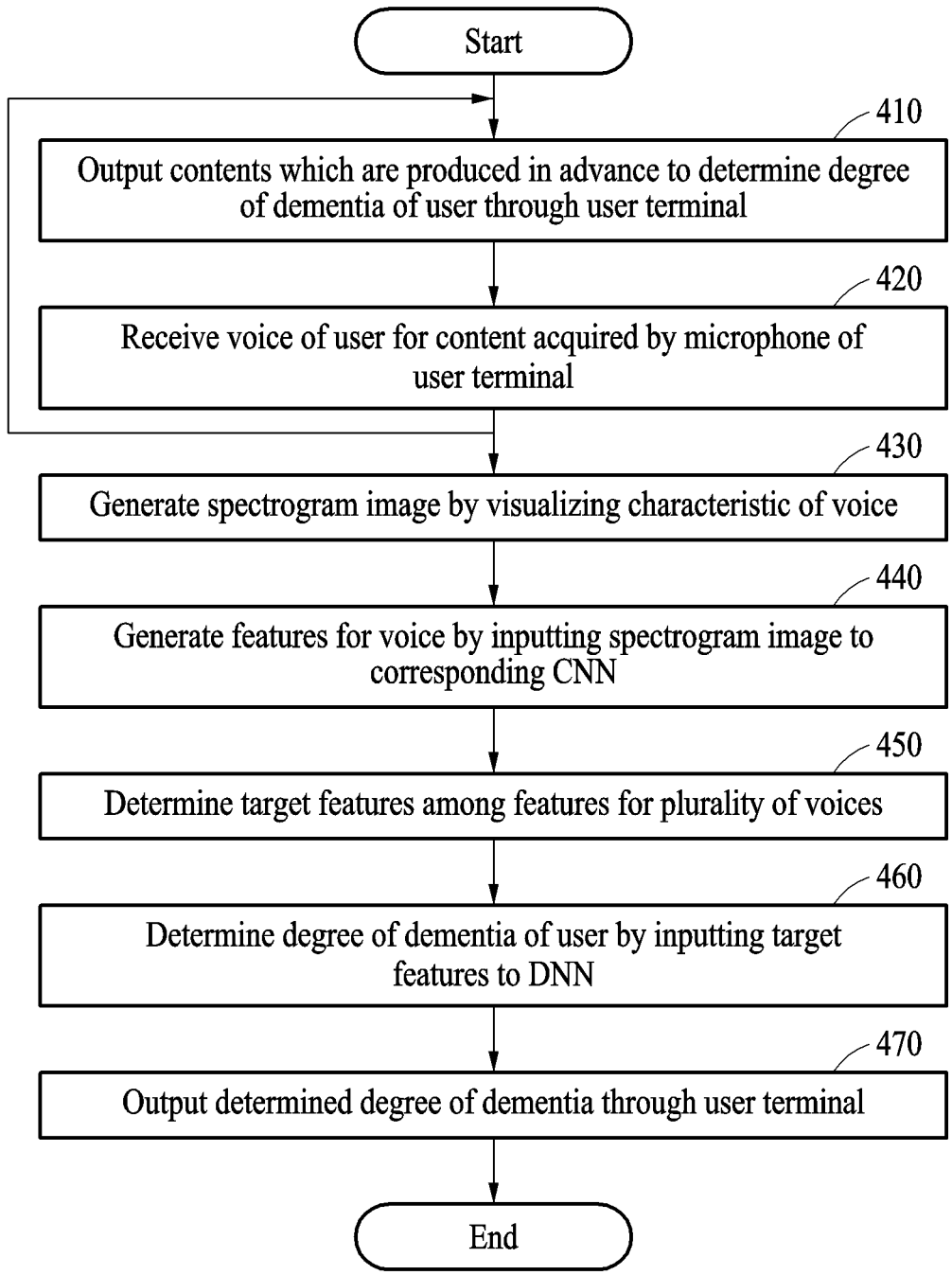
FIG. 4 is a flowchart of a method for determining a degree of dementia of a user according to an exemplary embodiment.

FIG. 4 is a flowchart of a method for determining a degree of dementia of a user according to an exemplary embodiment.

The following steps 410 to 450 are performed by the electronic device 300 which has been described above with reference to FIG. 3.

In step 410, the electronic device 300 outputs contents which have been produced in advance to determine a degree of dementia of the user through a user terminal (for example, the user terminal 120). The contents are output to the user terminal and the user performs a reaction for the contents. The user terminal may generate a voice as the reaction using the microphone. The generated voice may have a data file format.

A plurality of contents is provided to the user and a voice for each of the plurality of contents may be generated. The plurality of contents according to the example will be described using the following Table 1.

TABLE 1

| Voice task | Instructions |
| --- | --- |
| Step 1. Repeating Sentences | From now on, please listen carefully to the sentences I say and repeat them. After listening to each sentence, begin speaking when you hear a beep. In the yard, Roses, Bloomed. |
| Step 2. Repeating Sentences | Again, please listen carefully to the sentences I say and repeat them. After listening to each sentence, begin speaking when you hear a beep. Yesterday, It rained, I Stayed, Home. |
| Step 3. Repeating Sentences | Again, please listen carefully to the sentences I say and repeat them. After listening to each sentence, begin speaking when you hear a beep. Walls have ears. |
| Step 4. Naming | Next, you will say the name of the animals you see. When you hear a beep, say the names of the animals you see in the order one by one. |
| Step 5. Describing Pictures | Next, look at the picture, and explain the picture, in as much detail as possible, for one minute. Please explain in as much detail as possible about where the place is, what things there are, what animals or people are doing, etc. Start when you hear a beep. |
| Step 6. Language Fluency (phoneme) | Next is saying words that begin with the letter I give you. For example, if I give you the letter "A," tell me as many words you can that begin with the letter "A." You can say words like Apple, America, Alarm. Are there any other words that begin with the letter A? Next, tell me words that begin with a different letter, the letter "B." I will give you one minute. Say as many words as you can that start with the letter "B." Are you ready? Start when you hear a beep. |

TABLE 1-continued

| Voice task | Instructions |
| --- | --- |
| Step 7. Language Fluency (Meaning) | If I tell you a category, please tell me the names of the things that belong to that category as soon as possible. For example, if I say 'kinds of animals,' you can say things like dog, cat, lion, etc. Are there other things that belong to the category, animals? From now on, tell me all the names of things that belong in a different category, fruit. I'll give you one minute. Within one minute, name all the names of fruits that come to mind. Are you ready? Start when you hear a beep. |
| Step 8. Subtracting Numbers | Now, it's a simple calculation problem. If you subtract 3 from 100, what is it? If you subtract 3 from 100, you get 97. So, then, subtract another 3 from there. Subtract 3 from 97, so the answer is 94. So you keep subtracting 3. Start at 100, and keep subtracting 3, are you ready? Start when you hear a beep. |
| Step 9. Storytelling (Positive) | What has been the happiest thing in your life so far? Please tell me about the happiest thing in your life, in as much detail as possible for one minute. Start when you hear a beep. |
| Step 10. Storytelling (Negative) | What has been the saddest thing in your life so far? Please tell me about the saddest thing in your life, in as much detail as possible for one minute. Start when you hear a beep. |
| Step 11. Storytelling (Illustration) | Can you tell me what you did yesterday? Tell me about what happened yesterday, in as much detail as possible for one minute. Start when you hear a beep. |

In step 420, the electronic device 300 receives a voice of the user for the contents acquired through the microphone of the user terminal. When a plurality of contents is provided, a plurality of voices may be received.

When a plurality of contents is produced, steps 410 and 420 may be repeated. The steps 410 and 420 are repeated so that the voices for the plurality of contents are received. For example, when the plurality of contents includes first to eleventh contents, first to eleventh voices corresponding to the contents are received.

In step 430, the electronic device 300 generates a spectrogram image for the voice by visualizing at least one characteristic of the received voice. For example, the electronic device 300 may generate a spectrogram image for the voice through a librosa tool. The spectrogram image may be a mel-spectrogram image.

For example, first to eleventh spectrogram images for the first to eleventh voices may be generated. The spectrogram image will be described below in detail with reference to FIG. 7.

In step 440, the electronic device 300 generates a predetermined number of features for the voice by inputting the spectrogram image to a previously updated convolutional neural network (CNN) corresponding to the spectrogram image. The CNN used to generate the features may vary depending on the contents. For example, when there are eleven contents, there are CNNs corresponding to eleven contents and eleven CNNs may be referred to as a CNN set. Hereinafter, the term "updating" may include a meaning of "training" and both terms may be interchangeably used.

According to an aspect, the CNN may be updated in advance based on a VGG16 model. The CNN may be a part of a fully CNN including one input layer, one or more convolution layer blocks, a fully connected layer, and a softmax. For example, the CNN may include the input layer and the one or more convolution layer blocks, but may not include the fully connected layer and the softmax. Since the CNN does not include the fully connected layer and the softmax, as a result for the input spectrogram image, rather than the degree of dementia, a predetermined number of features used to calculate a degree of dementia may be output. The fully CNN and the partially CNN will be described in detail with reference to FIG. 8.

For example, the electronic device 300 inputs a first spectrogram image to a previously updated first CNN to generate a predetermined number of first features for the first voice and inputs a second spectrogram image to a previously updated second CNN to generate a predetermined number of second features for the second voice. As a specific example, when eleven voices are received and 4608 features are generated for one voice, a total of 50688 features may be generated.

In step 450, the electronic device 300 determines target features among features for the plurality of voices. The determined target features may be markers for dementia diagnosis. As a specific example, ten features, among a total of 50,688 features, may be determined. Features determined as target features may be determined in advance as markers. The marker may be determined in advance by means of a step of updating a CNN and a step of updating a deep neural network (DNN) which will be described below with reference to FIGS. 12 to 16.

In step 460, the electronic device 300 inputs the target features to the previously updated DNN to determine the degree of dementia of the user. For example, the determined degree of dementia may be a normal state or an abnormal state. The abnormal state may include a mild cognitive impairment (MCI) or Alzheimer's disease (AD). In order to more precisely determine the degree of dementia of the user, two classification steps may be performed. Hereinafter, the two classification steps which are performed to increase the accuracy of determining a degree of dementia will be described.

In step 470, the electronic device 300 outputs the determined degree of dementia through the user terminal.

Figure 5:
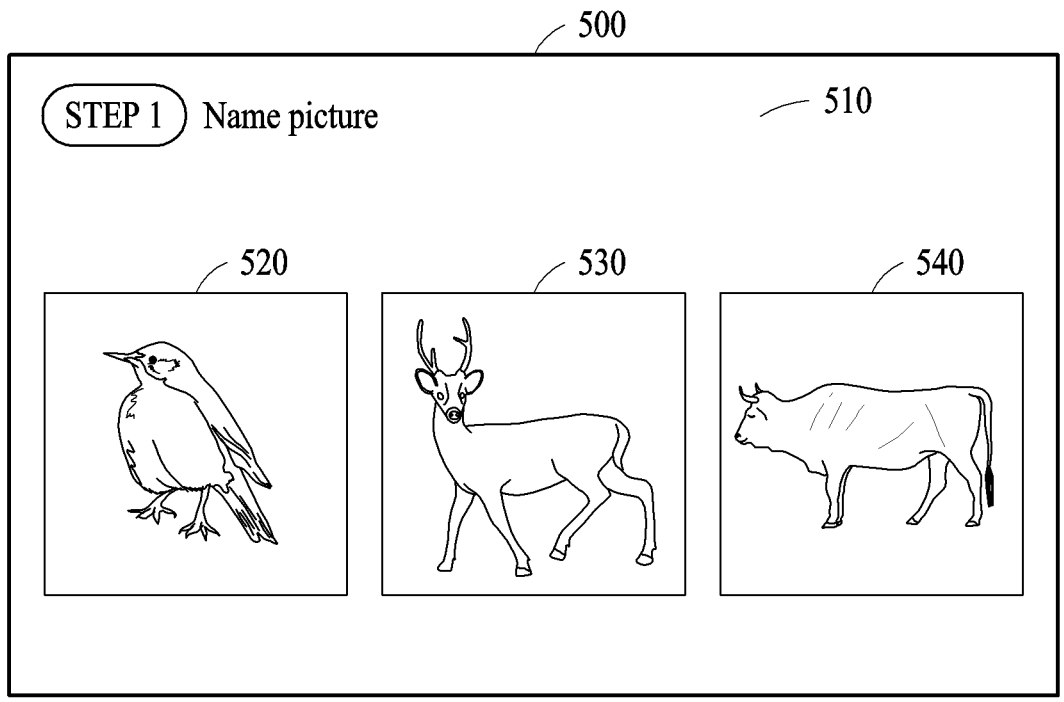
FIG. 5 illustrates contents which have been produced in advance according to an example.

FIG. 5 illustrates contents which have been produced in advance according to an example.

For example, the contents 500 provided to the user may be contents for telling names of output images 520, 530, and 540. The contents 500 may include an instruction 510 for the voice of the user with respect to the contents 500 in addition to the images 520, 530, and 540. The instruction 510 may be represented by a text or output as a voice. The user may say the names of the images 520, 530, and 540 to generate a voice.

Figure 6:
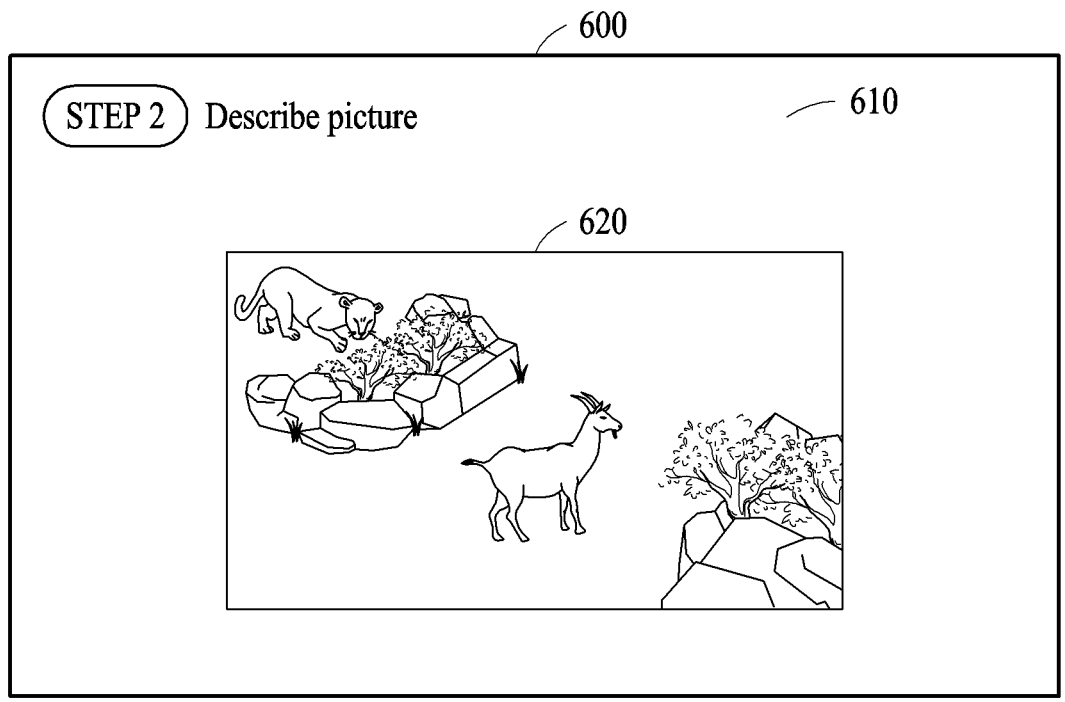
FIG. 6 illustrates contents which have been produced in advance according to another example.

FIG. 6 illustrates contents which have been produced in advance according to another example.

As a different example from the example of FIG. 5, the contents 600 provided to the user may be contents for explaining an output image 620. The contents 600 may include an instruction 610 for the voice of the user with respect to the contents 600 in addition to the image 620. The instruction 610 may be represented by a text or output as a voice. The user may generate the voice by explaining or describing the situation of the image 620.

Figure 7:
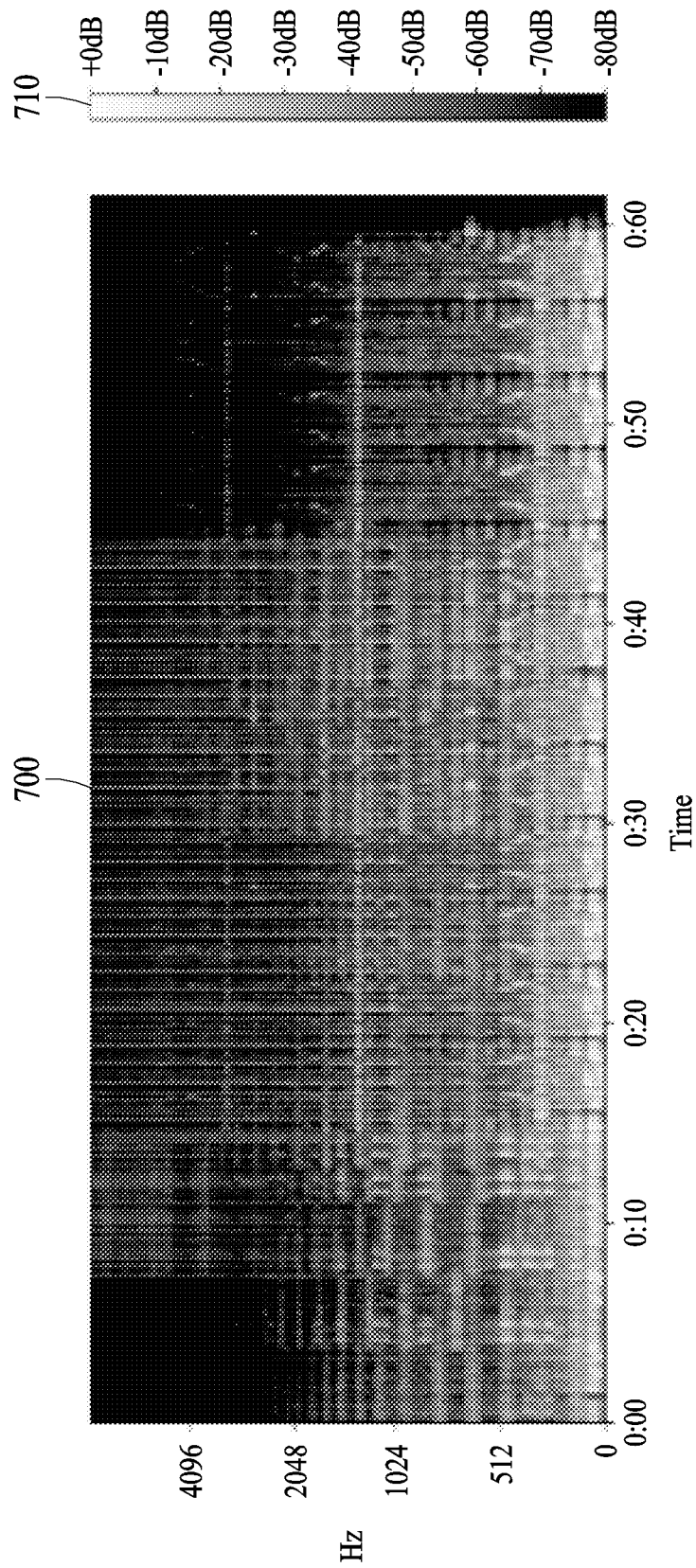
FIG. 7 illustrates a spectrogram image generated for a voice according to an example.

FIG. 7 illustrates a spectrogram image generated for a voice according to an example.

According to an aspect, the electronic device 300 may generate the spectrogram image 700 for the voice through the librosa tool. A horizontal axis of the spectrogram image 700 is a time axis and a vertical axis is a frequency axis. The spectrogram image 700 represents a difference of an amplitude with a difference of a printed concentration/displayed color according to the changes in the time axis and the frequency axis. The displayed color of the corresponding position may be determined based on a magnitude of the changed amplitude difference. For example, remarks 710 of the displayed color with respect to the magnitude of the amplitude difference may be output together with the spectrogram image 700. Values of R, G, B channels of a pixel of the corresponding coordinate may be determined to display the determined color.

A plurality of spectrogram images for the plurality of voices may be generated. For example, a first spectrogram image for the first voice may be generated and a second spectrogram image for the second voice may be generated. Scales of the time axis and the frequency axis of the spectrogram image may vary depending on a total time of the individual voice, but the sizes of the generated spectrogram images may be equal to each other. For example, a size of the first spectrogram image and a size of the second spectrogram image are 100×100 which are equal to each other.

Figure 8:
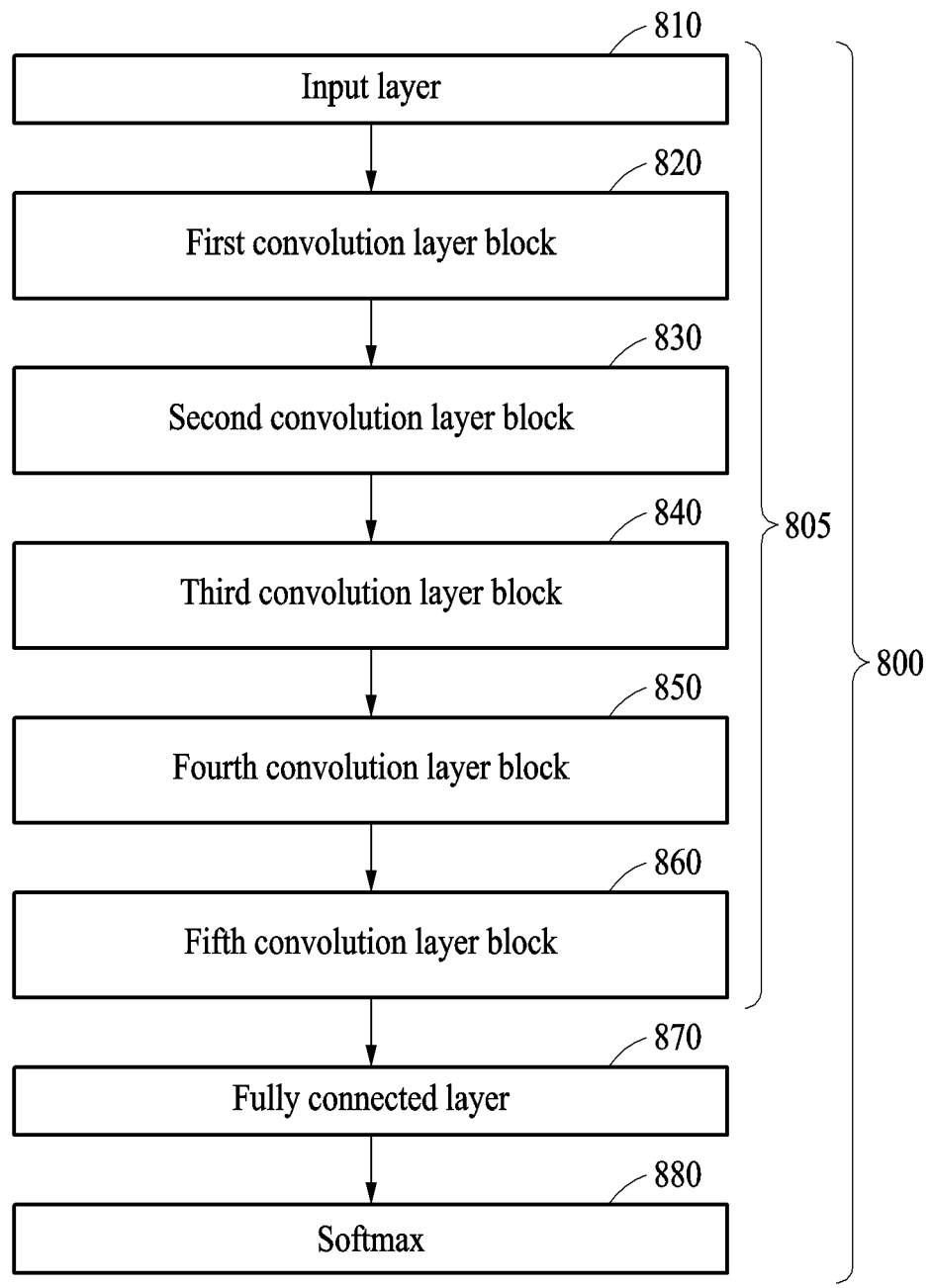
FIG. 8 illustrates a fully CNN and a partially CNN which determine a degree of dementia of a user according to an example.

FIG. 8 illustrates a fully CNN and a partially CNN which determine a degree of dementia of a user according to an example.

According to an aspect, the fully CNN 800 includes an input layer 810, a first convolution layer block 820, a second convolution layer block 830, a third convolution layer block 840, a fourth convolution layer block 850, a fifth convolution layer block 860, a fully connected layer 870, and a softmax 880. The convolution layer block may include one or more convolution layers and a pooling layer.

The fully CNN 800 may be a fully CNN which is updated by the fully CNN updating method to be described below with reference to FIG. 12. Different CNNs for every content may be updated in advance.

The partially CNN 805 includes only the input layer 810, the first convolution layer block 820, the second convolution layer block 830, the third convolution layer block 840, the fourth convolution layer block 850, and the fifth convolution layer block 860, but may not include a fully connected layer 870 and a softmax 880. That is, the partially CNN 805 may be a CNN obtained by removing the fully connected layer 870 and the softmax 880 from the fully CNN 800 after completing the updating of the fully CNN 800. For example, the CNN used in the step 440 described above with reference to FIG. 3 may be a partially CNN 805.

The partially CNN 805 does not include the fully connected layer 870 so that the partially CNN 805 may output various features for the spectrogram image.

Figure 9:
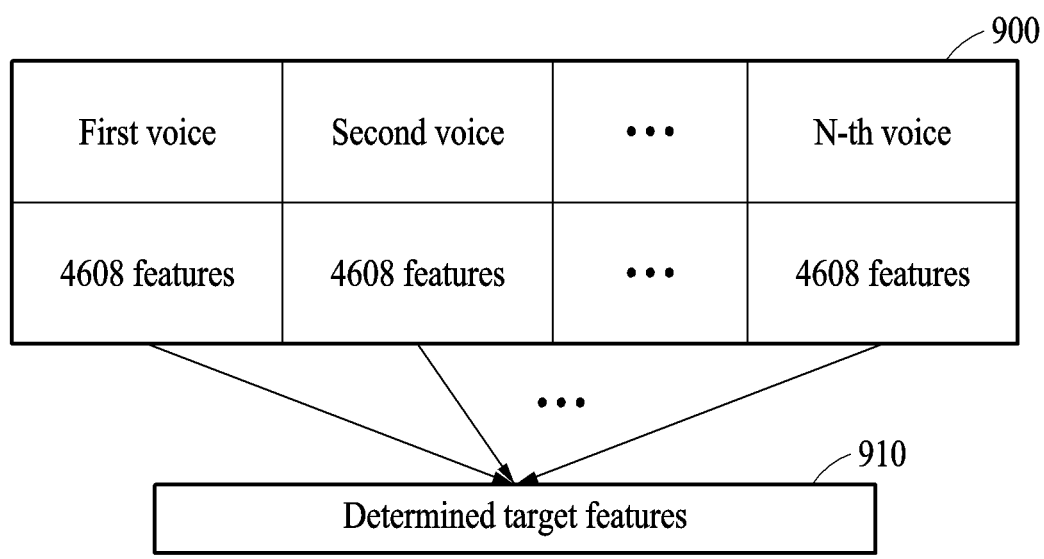
FIG. 9 illustrates features generated for each of a plurality of voices according to an example and target features determined based thereon.

FIG. 9 illustrates features generated for each of a plurality of voices according to an example and target features determined based thereon.

According to an aspect, a predetermined number of features for the target voice is generated through the target CNN corresponding to the target voice. For example, the predetermined number of features may be 4608. When the number of voices is n, the number of total generated features 900 may be 4608×n.

Among all the features 900, a predetermined number of target features 910 is determined. The determined target features 910 may be a marker which is set in advance to determine a degree of dementia. A method for determining the target features 910 in advance as a marker will be described below in detail with reference to step 1310 of FIG. 13.

Figure 10:
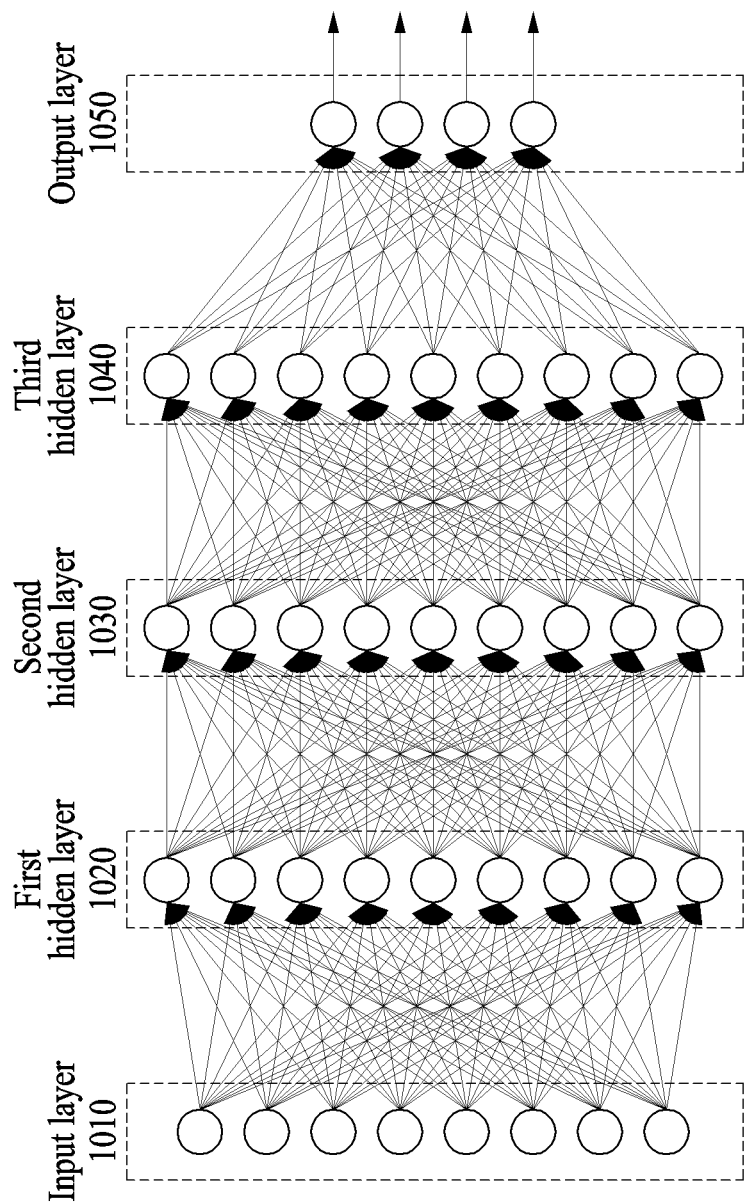
FIG. 10 illustrates a DNN of determining a degree of dementia of a user according to an example.

FIG. 10 illustrates a DNN of determining a degree of dementia of a user according to an example.

According to an aspect, the DNN which determines a degree of dementia of the user may include an input layer 1010, one or more hidden layers 1020, 1030, 1040, and an output layer 1050. For example, the DNN may be a DNN which is updated by a method of updating a DNN to be described below with reference to FIG. 13.

The DNN may output a degree of dementia of the user as an output for an input of the target features 910. The DNN may output any one of a plurality of predetermined degrees of dementia. For example, the plurality of predetermined degrees of dementia may include a determined normal state, mild cognitive impairment (MCI), and Alzheimer's disease (AD).

Figure 11:
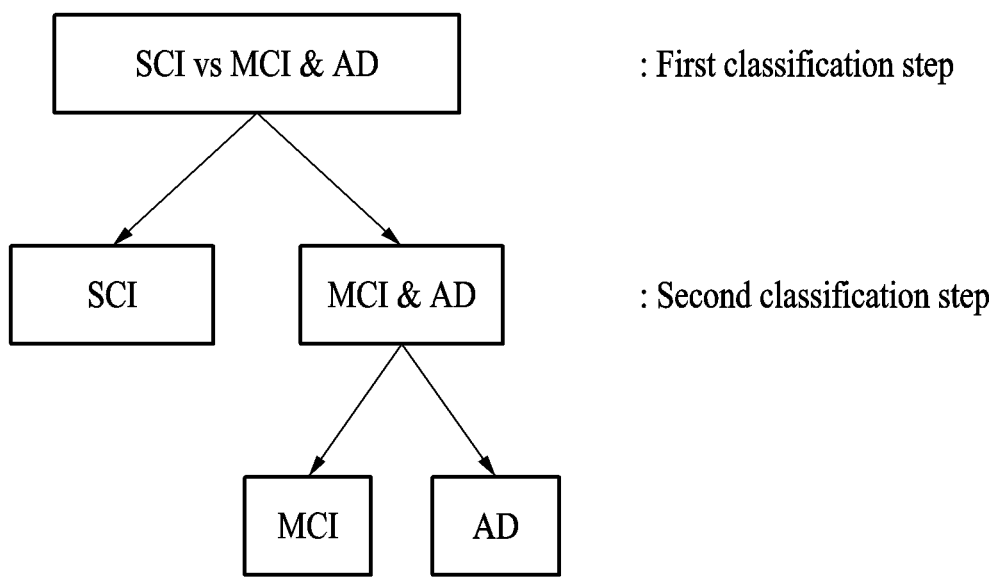
FIG. 11 illustrates two classification steps performed to increase an accuracy of determining a degree of dementia according to an example.

FIG. 11 illustrates two classification steps performed to increase an accuracy of determining a degree of dementia according to an example.

The accuracy of determining a degree of dementia may be increased by a method of determining a degree of dementia through a plurality of models step by step, rather than a method of determining any one of a plurality of degrees of dementia by one model.

For example, rather than the method of determining any one of a normal state, mild cognitive impairment (MCI), and Alzheimer's disease (AD) by one model, a normal state or an abnormal state (mild cognitive impairment (MCI) and Alzheimer's disease (AD)) may be determined in a first classification step, and the mild cognitive impairment (MCI) or the Alzheimer's disease (AD) may be determined in a second classification step.

In order to use the above-described method, a first CNN set and a first DNN set used for the first classification step and a second CNN set and a second DNN set used for the second classification step are prepared in advance.

For example, steps 410 to 460 are performed for the first classification step, and when the degree of dementia of the user is determined to be abnormal in the first classification step, steps 440 to 470 for the second classification step may be performed. When the degree of dementia of the user is determined to be normal in the first classification step, the second classification step may not be performed. The first CNN set and the first DNN set used for the first classification step and the second CNN set and the second DNN set used for the second classification step are different from each other.

Figure 12:
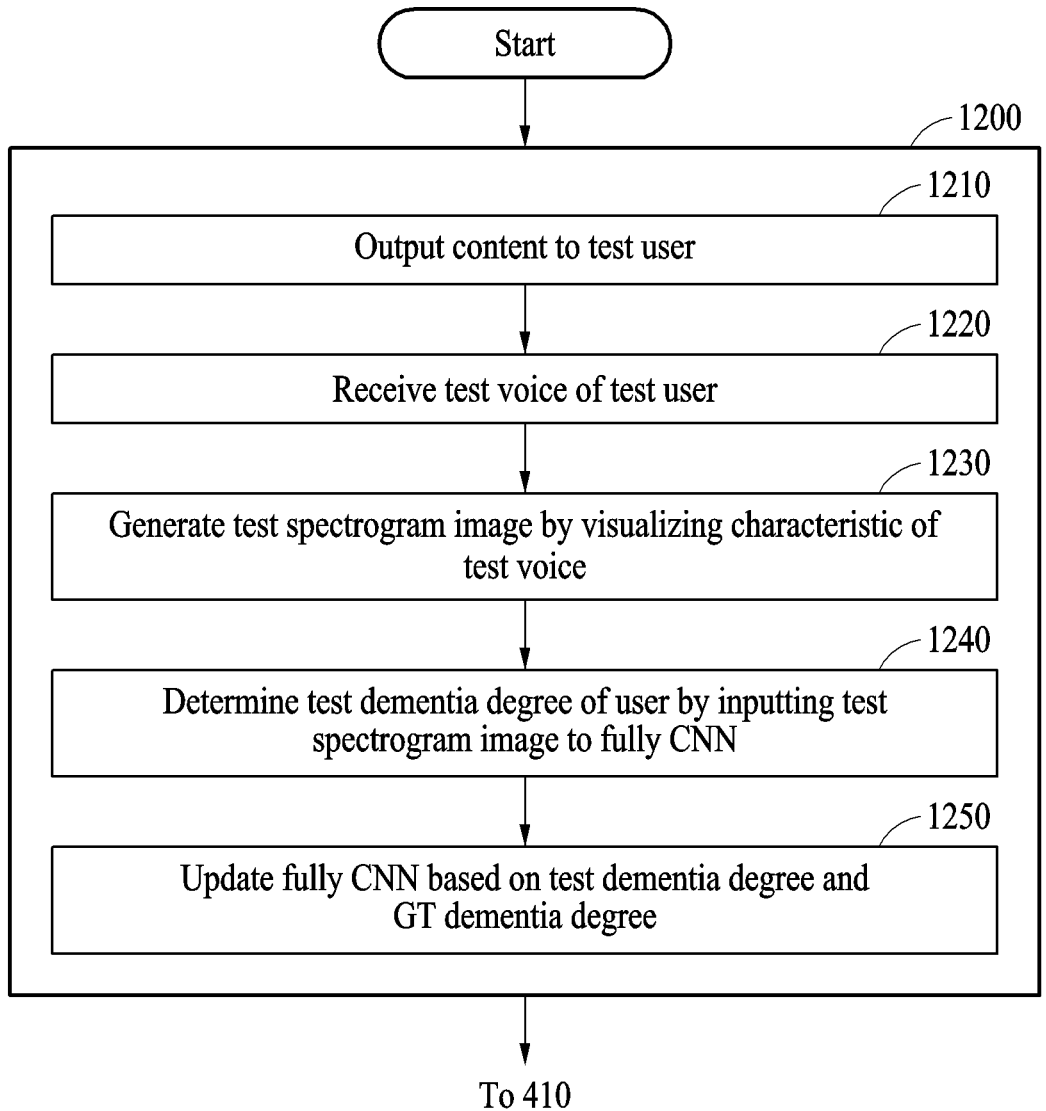
FIG. 12 is a flowchart of a method of updating a fully CNN according to an example.

FIG. 12 is a flowchart of a method of updating a fully CNN according to an example.

According to an aspect, prior to performing the step 410 described above with reference to FIG. 4, the following step 1200 is precedently performed. The step 1200 relates to a method for updating the fully CNN and may include the following steps 1210 to 1250.

In step 1210, the electronic device 300 outputs contents which are produced in advance to determine a degree of dementia of the user to a test user. For example, the electronic device 300 may output contents through a user terminal of the test user.

The test user may be a person whose degree of dementia is determined by the specialized diagnosis of a doctor. For example, the test user may be normal or may have the mild cognitive impairment (MCI) or the Alzheimer's disease (AD).

In step 1220, the electronic device 300 receives a test voice of the test user for the contents acquired through the microphone of the user terminal. When a plurality of contents is provided, a plurality of test voices may be received.

In step 1230, the electronic device 300 generates a test spectrogram image for the test voice by visualizing at least one characteristic of the received test voice. A ground truth (GT) dementia degree of the test user may be labeled to the test spectrogram image.

In step 1240, the electronic device 300 inputs the test spectrogram image to the fully CNN to determine a test dementia degree for the test user. The fully CNN includes an input layer, one or more convolution layer blocks, a fully connected layer, and a softmax. For example, an initial version of the fully CNN may be a VGG 16 model.

The fully CNN includes the fully connected layer and the softmax, so that the fully CNN may determine a test dementia degree. For example, the determined test dementia degrees may include a normal state, the mild cognitive impairment (MCI), and the Alzheimer's disease (AD).

According to an aspect, the first fully CNN corresponding to a first content may determine a test dementia degree of the test user only based on a first test spectrogram image and the second fully CNN corresponding to a second content may determine a test dementia degree of the test user only based on a second test spectrogram image.

In step 1250, the electronic device 300 updates the fully CNN based on the test dementia degree and the GT dementia degree. For example, when there is a difference between the test dementia degree and the GT dementia degree, in order to update the fully CNN, a back propagation may be performed with the difference as an error value. The method of updating the fully CNN may be supervised learning.

In an exemplary embodiment of FIG. 8, when the fully CNN 800 includes the input layer 810, the first convolution layer block 820, the second convolution layer block 830, the third convolution layer block 840, the fourth convolution layer block 850, the fifth convolution layer block 860, the fully connected layer 870, and the softmax 880, only the third to fifth convolution layer blocks 840, 850, 860 may be updated, but the other layers may not be updated.

According to an aspect, the fully CNN may be repeatedly updated by means of a large number of test users and when an output accuracy of the updated fully CNN is equal to or higher than a predetermined threshold, the updating of the fully CNN may be completed.

According to an aspect, when the degree of dementia is determined step by step by the plurality of models as described in the method described above with reference to FIG. 11, the first fully CNN set and the second fully CNN set used in each classification step may be individually updated to be suitable for each classification step. For example, the first fully CNN set may be updated to determine a normal state or an abnormal state (the mild cognitive impairment (MCI) and the Alzheimer's disease (AD)) and the second fully CNN set may be updated to determine the mild cognitive impairment (MCI) or the Alzheimer's disease (AD).

The CNN used in step 440 may be a neural network obtained by removing the fully connected layer and the softmax from the fully CNN after completing the updating of the fully CNN. That is, the CNN used in the step 440 may be used as a feature extractor of the spectrogram image.

Figure 13:
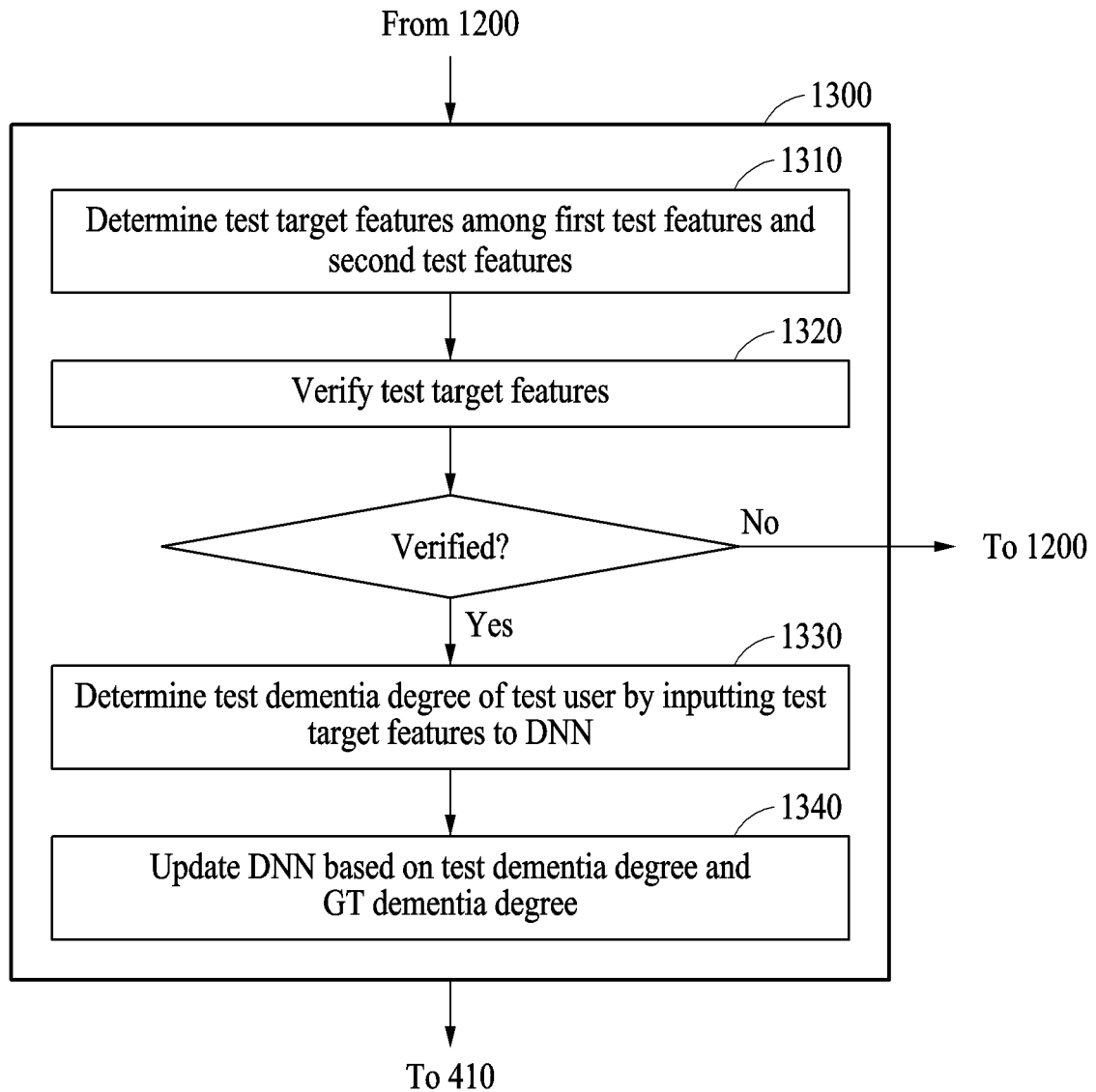
FIG. 13 is a flowchart of a method of updating a DNN according to an example.

FIG. 13 is a flowchart of a method of updating a DNN according to an example.

According to an aspect, the following step 1300 relates to a method for updating a DNN and may be precedently performed after performing the step 1200 described above with reference to FIG. 12 and before performing the step 410 described above with reference to FIG. 4. For example, the step 1300 may be performed after completing the updating of the fully CNN (or CNN).

The step 1300 may include the following steps 1310 to 1340.

In step 1310, the electronic device 300 determines a predetermined number of test target features among a predetermined number of first test features generated by the first CNN based on the first test spectrogram image and a predetermined number of second test features generated by the second CNN based on the second test spectrogram image. Although only the first test features and the second test features are described, for example, when n test spectrogram images for n contents are generated, the test target features may be determined among first test features to n-th test features. The test target features may be a marker used to determine a degree of dementia. A method for determining test target features will be described below in detail with reference to FIGS. 14 and 15.

A GT dementia degree of the test user may be labeled to the test target features. In step 1320, the electronic device 300 may verify the determined test target features. For example, the test target features may be verified by a K-fold cross-validation method.

A method for verifying test target features will be described below in detail with reference to FIGS. 15 and 16.

When the test target features are verified, step 1330 may be performed. When the test target features are not verified, it is considered that the re-updating of the CNN is necessary to re-perform the step 1200.

In step 1330, the electronic device 300 inputs the test target features to the DNN to determine the test dementia degree of the test user. In order to distinguish from the test dementia degree determined in the step 1240, the test dementia degree in step 1240 is referred to as a first test dementia degree and the test dementia degree in step 1330 is referred to as a second test dementia degree. When the step 1330 is initially performed, the used DNN may be an initial DNN or a basic DNN.

In step 1340, the electronic device 300 updates the DNN based on the second test dementia degree and the GT degree dementia. For example, when there is a difference between the second test dementia degree and the GT dementia degree, in order to update the DNN, a back propagation may be performed with the difference as an error value. The method of updating the DNN may be supervised learning.

According to an aspect, the DNN may be repeatedly updated by means of a large number of test users and when an output accuracy of the updated DNN is equal to or higher than a predetermined threshold, the updating of the DNN may be completed.

According to an aspect, when the degree of dementia is determined step by step by the plurality of models as described in the method described above with reference to FIG. 11, a first DNN and a second DNN used in each classification step may be individually updated to be suitable for each classification step. For example, the first DNN may be updated to determine a normal state or an abnormal state (the mild cognitive impairment (MCI) and the Alzheimer's disease (AD)) and the second DNN may be updated to determine the mild cognitive impairment (MCI) or the Alzheimer's disease (AD).

Figure 14:
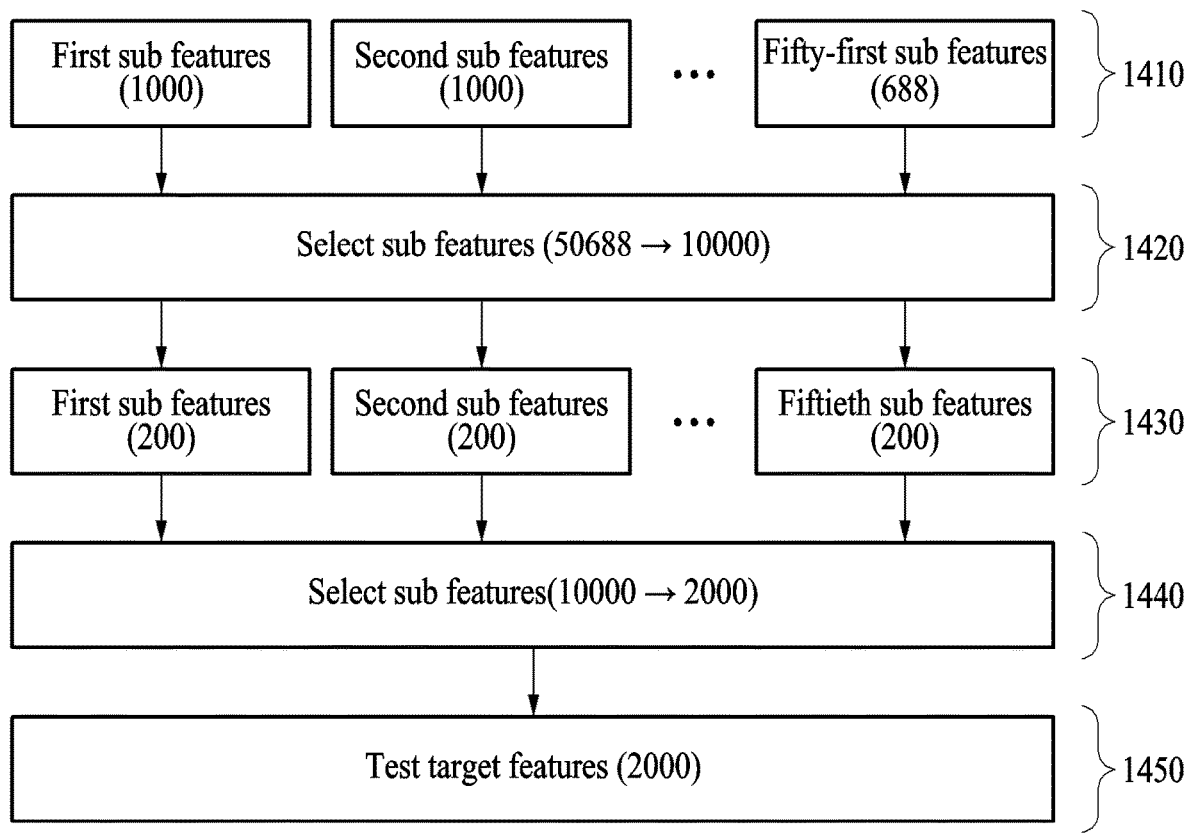
FIG. 14 is a flowchart of a method for determining test target features according to an example.

FIG. 14 is a flowchart of a method for determining test target features according to an example.

According to an aspect, the step 1310 which has been described above with reference to FIG. 13 may include the following steps 1410 to 1450.

In step 1410, the entire test features including the first test features and the second test features are divided into sets of a plurality of sub features. For example, when the entire test features are 50688, sets of sub features may be generated to include 1000 test features, respectively and a fifty-first set of sub features may include 688 test features. Each of the entire test features may have an index number and the first sub feature set includes a first test feature to 1000-th test feature.

In step 1420, some of sets (51 sets) of the plurality of sub features are selected. For example, 10 sets may be selected from the first sub feature set to the fifty-first sub feature set. The selected 10 sub feature sets include a total of 10000 test features. A method for selecting some of the sets of sub features will be described below in detail with reference to FIG. 15.

In step 1430, the selected sub features (for example, 10000 sub features) are divided into sets of a plurality of sub features. For example, when the selected features are 10000, sets (50 sets) of sub features may be generated to include 200 test features.

In step 1440, some of sets (50 sets) of the plurality of sub features are selected. For example, 10 sets may be selected from the first sub feature set to the fiftieth sub feature set. The selected 10 sets of sub features include a total of 2000 test features. The following description of FIG. 15 for the step 1420 may be similarly applied to the detailed description of the step 1440.

In step 1450, test features included in the selected sub feature sets are determined as test target features. Indexes of the determined test target features may be identified.

The determined test target features may be used as a marker for determining a degree of dementia of the user. For example, when a fifty-sixth feature, 100-th feature, and 760-th feature among the first features and a first feature and 2400-th feature among the second features are determined as test target features, the target features determined in the step 450 described above with reference to FIG. 4 include a fifty-sixth feature, 100-th feature, and 760-th feature among the first features and a first feature and 2400-th feature among the second features.

Figure 15:
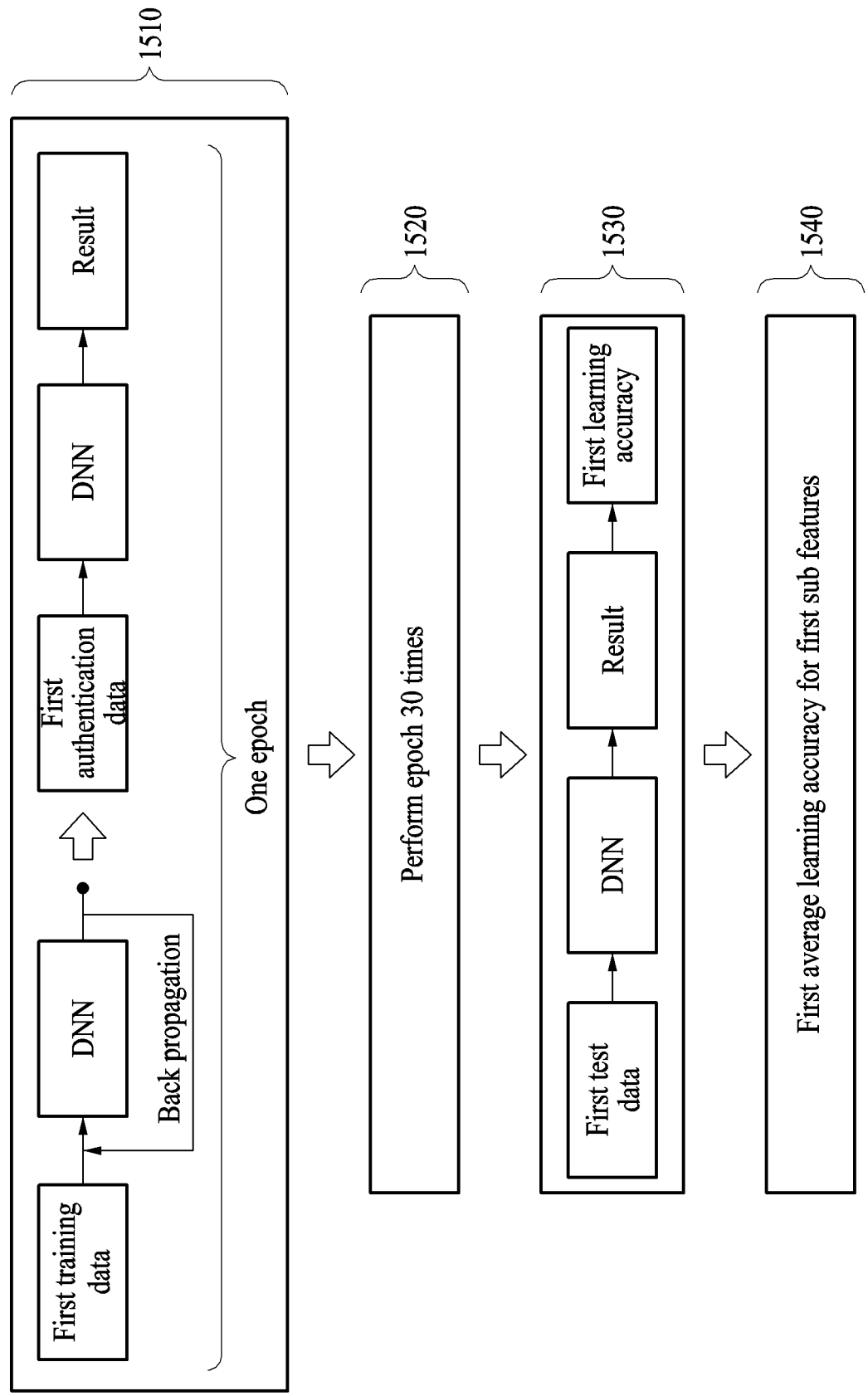
FIG. 15 is a flowchart of a method for selecting sub features according to an example.

FIG. 15 is a flowchart of a method for selecting sub features according to an example.

According to an aspect, the step 1420 which has been described above with reference to FIG. 14 may include the following steps 1510 to 1540.

In order to determine the test target features, data for a large number of users is required. A process of determining test target features with data for 1000 users as an example will be described below. Data for 1000 users is set with a correct answer value.

For example, 1000 users may be classified into 600 training data users, 200 authenticated data users, and 200 test data users. 50688 features for a first voice to eleventh voices for 600 users may be generated and 600 first sub feature sets having specific indexes (for example, 1 to 1000) may be generated. For example, 600 first sub feature sets to fifty-first sub feature sets for the training data are generated. Similarly, 200 first sub feature sets to fifty-first sub feature sets for the authenticated data are generated and 200 first sub feature sets to fifty-first sub feature sets for the test data are generated In step 1510, one epoch for the initial DNN is performed based on 600 first sub feature sets (first training data) of the training data and 200 first sub feature sets (first authenticated data) of the authenticated data. An edge of a node in the DNN or a weight of a parameter is adjusted based on 600 first sub feature sets. A result for the first authenticated data input through the DNN with adjusted weight is output. 200 results may be output. An administrator may adjust a predetermined number of epochs performed for learning by referring to 200 output results.

In step 1520, a predetermined number of epochs is performed for the DNN. For example, 30 epochs may be performed. When the predetermined number of epochs is performed, it is considered that one learning (or training) is completed.

In step 1530, a first learning accuracy may be calculated based on 200 first sub feature sets (first test data) of the test data. For example, the first test data is input to the trained DNN and the accuracy for 200 results may be calculated as a first learning accuracy.

A predetermined number of times of steps 1510 to 1530 is repeated to calculate additional learning accuracies. Since the initial DNNs provided in step 1510 are different from each other, the results of the DNN learning may vary so that the learning accuracies for a plurality of the number of times of learning may vary. When the steps 1510 to 1530 are repeated 10 times, a first learning accuracy to a tenth learning accuracy may be calculated.

In step 1540, a first average learning accuracy for the first training data is calculated. For example, an average for the first learning accuracy to the tenth learning accuracy may be calculated as a first average learning accuracy.

For example, when the steps 1510 to 1540 are performed for the first sub feature set including features with indexes 1 to 1000, the first average learning accuracy for the first sub feature set may be calculated.

As another example, when the steps 1510 to 1540 are performed for the second sub feature set including features with indexes 1001 to 2000, the second average learning accuracy for the second sub feature set may be calculated.

A first average learning accuracy to a fifty-first average learning accuracy for each of 51 sub feature sets may be calculated. Upper ten sub feature sets among 51 average learning accuracies may be selected.

As another example, 51 sub feature sets are classified into a predetermined number of groups and a group average learning accuracy for a corresponding group may be calculated. Some of the plurality of groups are selected based on the group average learning accuracy to select the sub feature sets in the selected groups.

When ten sub feature sets are selected, 10000 indexes are selected. Since the selection is made for every sub feature set, a geographical characteristic between features generated by the CNN based on the spectrogram image may be automatically considered.

The description for the steps 1510 to 1540 may be applied similarly as a detailed description for the step 1440.

Figure 16:
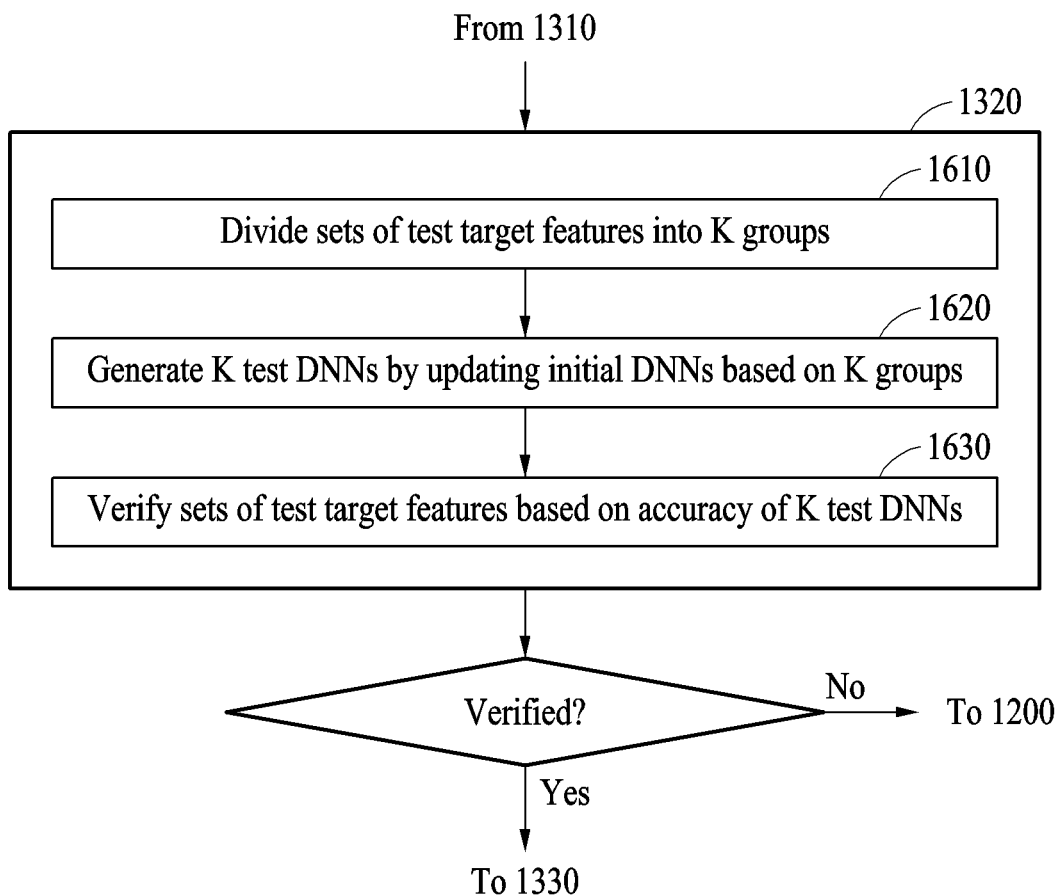
FIG. 16 is a flowchart of a method for verifying test target features according to an example.

FIG. 16 is a flowchart of a method for verifying test target features according to an example.

According to an aspect, the step 1320 which has been described above with reference to FIG. 13 may include the following steps 1610 to 1630.

In step 1610, the electronic device 300 may divide sets of the test target features into K groups. Test target features determined for each of the test users are defined as one set. For example, when there are 1000 test users, there are 1000 sets of test target features and 1000 sets are divided into K groups. K is a natural number of 2 or larger. When K is 5, five groups including 200 sets may be generated.

In step 1620, the electronic device 300 updates initial DNNs based on K groups to generate K test DNNs. When first to fifth groups are generated, a first test DNN is updated using second to fifth groups, a second test DNN is updated using first, third to fifth groups, a third test DNN is updated using first, second, fourth, and fifth groups, a fourth test DNN is updated using first to third and fifth groups, and a fifth test DNN is updated using first to fourth groups.

In step 1630, the electronic device 300 verifies the test target features based on the accuracy of K test DNNs. In the above exemplary embodiment, the first group is input to the first DNN to output a result for the first group and calculate a first accuracy of the output result. Similarly, second to fourth accuracies for the second to fourth test DNNs may be calculated.

When an average value of the calculated first to fifth accuracies is equal to or higher than a predetermined threshold, it may be determined that the test target features are verified. When an average value of the calculated first to fifth accuracies is lower than a predetermined threshold, it may be determined that the test target features are not verified. When the test target features are not verified, the CNN of extracting test features may be re-updated.

Figure 17:
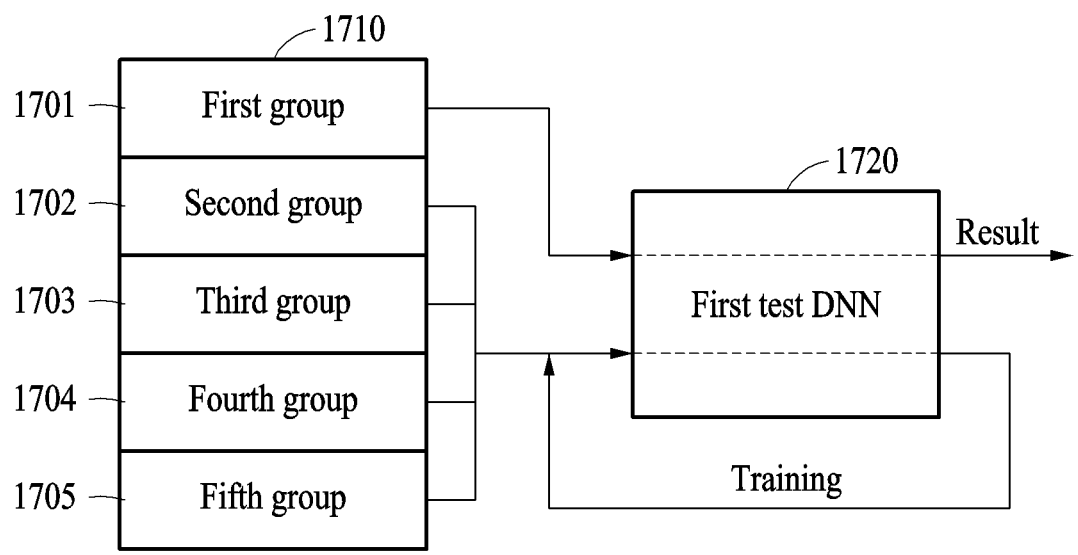
FIG. 17 illustrates a K-fold cross-validation for verifying target features according to an example.

FIG. 17 illustrates a K-fold cross-validation for verifying target features according to an example.

According to an example, sets 1710 of the test target features may be divided into a first group 1701, a second group 1702, a third group 1703, a fourth group 1704, and a fifth group 1705. When the test target feature sets 1710 includes 1000 sets, each of the groups 1701 to 1705 includes 200 sets. Each set includes test target features for a specific test user.

A first test DNN 1720 may be updated using second to fifth groups 1702 to 1705. For example, the first test DNN 1720 may be updated 800 times based on 800 sets.

The updated first test DNN 1720 may determine degrees of dementia of test users for the first group 1701 with the first group 1701 as an input. For example, the first test DNN 1720 may determine 200 second test dementia degrees for 200 sets.

The accuracy of the first test DNN 1720 may be calculated based on GT dementia degrees of each of 200 sets of the first group 1701 and 200 second test dementia degrees. Similarly, the accuracies of the second to fourth test DNNs may be calculated. Finally, the test target features may be verified based on an average of accuracies of the first to fifth test DNNs.

The device described above may be implemented by a hardware component, a software component, and/or a combination of the hardware component and the software component. For example, the device and the components described in the exemplary embodiments may be implemented, for example, using one or more general purpose computers or special purpose computers such as a processor, a controller, an arithmetic logic unit (ALU), a digital signal processor, a microcomputer, a field programmable array (FPA), a programmable logic unit (PLU), a microprocessor, or any other device which executes or responds instructions. The processing device may perform an operating system (OS) and one or more software applications which are performed on the operating system. Further, the processing device may access, store, manipulate, process, and generate data in response to the execution of the software. For ease of understanding, it may be described that a single processing device is used, but those skilled in the art may understand that the processing device includes a plurality of processing elements and/or a plurality of types of processing elements. For example, the processing device may include a plurality of processors or include one processor and one controller. Further, another processing configuration such as a parallel processor may be allowed.

The software may include a computer program, a code, an instruction, or a combination of one or more of them and configure the processing device to be operated as desired or independently or collectively instruct the processing device. The software and/or data may be permanently or temporarily embodied in an arbitrary type of machine, component, physical device, virtual equipment, computer storage medium, or device, or signal wave to be transmitted to be interpreted by a processing device or provide instruction or data to the processing device. The software may be distributed on a computer system connected through a network to be stored or executed in a distributed manner. The software and data may be stored in one or more computer readable recording media.

The method according to the example embodiment may be implemented as a program instruction which may be executed by various computers to be recorded in a computer readable medium. The computer readable medium may include solely a program instruction, a data file, and a data structure or a combination thereof. The program instruction recorded in the medium may be specifically designed or constructed for the example embodiment or known to those skilled in the art of a computer software to be used. An example of the computer readable recording medium includes magnetic media, such as a hard disk, a floppy disk, and a magnetic tape, optical media, such as a CD-ROM and a DVD, magneto-optical media, such as a floptical disk, and a hardware device, such as a ROM, a RAM, a flash memory, specially formed to store and execute a program instruction. Examples of the program instruction include not only a machine language code which is created by a compiler but also a high level language code which may be executed by a computer using an interpreter. The hardware device may operate as one or more software modules in order to perform the operation of the example embodiment and vice versa.

Although the exemplary embodiments have been described above by a limited example and the drawings, various modifications and changes can be made from the above description by those skilled in the art. For example, even when the above-described techniques are performed by different order from the described method and/or components such as a system, a structure, a device, or a circuit described above are coupled or combined in a different manner from the described method or replaced or substituted with other components or equivalents, the appropriate results can be achieved.

Therefore, other implements, other exemplary embodiments, and equivalents to the claims are within the scope of the following claims.

The invention claimed is:

1. A method for determining a degree of dementia of a user, performed by an electronic device, the method comprising:
    outputting a first content which is produced in advance to determine a degree of dementia of a user through a user terminal;
    receiving a first voice of the user for the first content acquired by a microphone of the user terminal;
    outputting a second content which is produced in advance through the user terminal;
    receiving a second voice of the user for the second content acquired by the microphone;
    generating a first spectrogram image by visualizing at least one characteristic of the first voice;
    generating a second spectrogram image by visualizing at least one characteristic of the second voice;
    generating a predetermined number of first features for the first voice by inputting the first spectrogram image to a previously updated first convolutional neural network (CNN);
    generating a predetermined number of second features for the second voice by inputting the second spectrogram image to a previously updated second CNN;
    determining a predetermined number of target features among the first features and the second features; and
    determining the degree of dementia of the user by inputting the target features to a previously updated deep neural network (DNN), wherein the determined degree of dementia is output through the user terminal,
    wherein the first CNN is updated by:
        receiving a first test voice of a test user for the first content;
        generating a first test spectrogram image by visualizing at least one characteristic of the first test voice in which a ground truth (GT) dementia degree of the test user is labeled to the first test spectrogram image;
        determining a first test dementia degree of the test user by inputting the first test spectrogram image to a first fully CNN in which the first fully CNN includes an input layer, one or more convolution layer blocks, a fully connected layer, and a softmax; and
        updating the first fully CNN based on the first test dementia degree and the GT dementia degree, and
        the first CNN includes only the input layer and the one or more convolution layer blocks among layers of the updated first fully CNN.

2. The method for determining a degree of dementia according to claim 1, wherein the first content includes an instruction for receiving the first voice and the first content is one of a content of causing a user to repeat a sentence, a content of naming an output image, a content of describing an output image, a content for language fluency, a content for calculating numbers, and a content of leading story telling.

3. The method for determining a degree of dementia according to claim 1, wherein the generating of a first spectrogram image by visualizing at least one characteristic of the first voice includes:
    generating the first spectrogram image for the first voice by means of a librosa tool.

4. The method for determining a degree of dementia according to claim 1, wherein the first CNN is updated in advance based on a VGG16 model.

5. The method for determining a degree of dementia according to claim 1, wherein the first CNN includes an input layer and five convolution layer blocks, but does not include a fully connected layer and a softmax to generate the first features for the first spectrogram image.

6. The method for determining a degree of dementia according to claim 1, further comprising:
    updating the DNN after completing the updating of a plurality of CNNs including the first CNN and the second CNN.

7. The method for determining a degree of dementia according to claim 6, wherein the updating of the DNN includes:
    determining a predetermined number of test target features among a predetermined number of first test features generated based on a first test spectrogram image and a predetermined number of second test features generated based on a second test spectrogram image in which the GT dementia degree of the test user is labeled to the test target features;
    determining a second test dementia degree of the test user by inputting the test target features to the DNN; and
    updating the DNN based on the second test dementia degree and the GT dementia degree.

8. The method for determining a degree of dementia according to claim 7, wherein the updating of the DNN further includes:
verifying the test target features by means of a K-fold cross-validation in which K is a natural number of 2 or larger, and
when the test target features are not verified, the first CNN and the second CNN are re-updated.

9. The method for determining a degree of dementia according to claim 8, wherein the verifying of the test target features by means of a K-fold cross-validation includes:
dividing sets of the test target features into K groups;
generating K test DNNs by updating K initial DNNs, respectively, based on the K groups; and
verifying the test target features based on an accuracy of the K test DNNs.

10. A computer readable recording medium which stores a program executing the method according to claim 1.

11. An electronic device for determining a degree of dementia of a user, the electronic device comprising:
a memory in which a program of determining a degree of dementia of a user is recorded; and
a processor which executes the program,
wherein the program executes:
outputting a first content which is produced in advance to determine the degree of dementia of the user through a user terminal;
receiving a first voice of the user for the first content acquired by a microphone of the user terminal;
outputting a second content which is produced in advance through the user terminal;
receiving a second voice of the user for the second content acquired by the microphone;
generating a first spectrogram image by visualizing at least one characteristic of the first voice;
generating a second spectrogram image by visualizing at least one characteristic of the second voice;
generating a predetermined number of first features for the first voice by inputting the first spectrogram image to a previously updated first convolutional neural network (CNN);
generating a predetermined number of second features for the second voice by inputting the second spectrogram image to a previously updated second CNN;
determining a predetermined number of target features among the first features and the second features; and
determining the degree of dementia of the user by inputting the target features to a previously updated deep neural network (DNN), and the determined degree of dementia is output through the user terminal,
wherein the first CNN is updated by:
receiving a first test voice of a test user for the first content;
generating a first test spectrogram image by visualizing at least one characteristic of the first test voice in which a ground truth (GT) dementia degree of the test user is labeled to the first test spectrogram image;
determining a first test dementia degree of the test user by inputting the first test spectrogram image to a first fully CNN in which the first fully CNN includes an input layer, one or more convolution layer blocks, a fully connected layer, and a softmax; and
updating the first fully CNN based on the first test dementia degree and the GT dementia degree, and the first CNN includes only the input layer and the one or more convolution layer blocks among layers of the updated first fully CNN.

12. A method for updating a convolutional neural network (CNN) used to determine a degree of dementia of a user, executed by an electronic device, the method comprising:
outputting a first content which is produced in advance to determine a degree of dementia of a user through a user terminal;
receiving a first test voice of a test user for the first content;
generating a first test spectrogram image by visualizing at least one characteristic of the first test voice in which a ground truth (GT) dementia degree of the test user is labeled to the first test spectrogram image;
determining a test dementia degree of the test user by inputting the first test spectrogram image to a fully CNN in which the fully CNN includes an input layer, one or more convolution layer blocks, a fully connected layer, and a softmax; and
updating the fully CNN based on the test dementia degree and the GT dementia degree,
wherein the CNN includes only the input layer and the one or more convolution layer blocks among layers of the updated fully CNN.

13. An electronic device which updates a convolutional neural network (CNN) used to determine a degree of dementia of a user, the electronic device comprising:
a memory in which a program of updating the CNN is recorded; and
a processor which executes the program,
wherein the program executes:
outputting a first content which is produced in advance to determine a degree of dementia of a user through a user terminal;
receiving a first test voice of a test user for the first content;
generating a first test spectrogram image by visualizing at least one characteristic of the first test voice in which a ground truth (GT) dementia degree of the test user is labeled to the first test spectrogram image;
determining a test dementia degree of the test user by inputting the first test spectrogram image to a fully CNN in which the fully CNN includes an input layer, one or more convolution layer blocks, a fully connected layer, and a softmax; and
updating the fully CNN based on the test dementia degree and the GT dementia degree, and
the CNN includes only the input layer and the one or more convolution layer blocks among layers of the updated fully CNN.

\* \* \* \* \*